US011925633B2

(12) United States Patent
Matsumoto et al.

(10) Patent No.: US 11,925,633 B2
(45) Date of Patent: Mar. 12, 2024

(54) DRUG FOR PREVENTING AND/OR TREATING DEMENTIA

(71) Applicant: NATIONAL CEREBRAL AND CARDIOVASCULAR CENTER, Suita (JP)

(72) Inventors: Tadamasa Matsumoto, Tokyo (JP); Masafumi Ihara, Suita (JP); Satoshi Saito, Suita (JP); Masanori Fukushima, Kobe (JP)

(73) Assignee: NATIONAL CEREBRAL AND CARDIOVASCULAR CENTER, Suita (JP)

( * ) Notice: Subject to any disclaimer, the term of this patent is extended or adjusted under 35 U.S.C. 154(b) by 319 days.

(21) Appl. No.: 17/126,488

(22) Filed: Dec. 18, 2020

(65) Prior Publication Data

US 2021/0100790 A1 Apr. 8, 2021

Related U.S. Application Data

(62) Division of application No. 16/302,097, filed as application No. PCT/JP2017/017195 on May 1, 2017, now abandoned.

(30) Foreign Application Priority Data

May 19, 2016 (JP) ................. 2016-100092

(51) Int. Cl.
*A61K 31/4709* (2006.01)
*A61K 31/353* (2006.01)
*A61P 25/28* (2006.01)

(52) U.S. Cl.
CPC ........ *A61K 31/4709* (2013.01); *A61K 31/353* (2013.01); *A61P 25/28* (2018.01)

(58) Field of Classification Search
None
See application file for complete search history.

(56) References Cited

U.S. PATENT DOCUMENTS

| | | | |
|---|---|---|---|
| 7,825,130 | B2 | 11/2010 | Hong |
| 8,329,731 | B2 | 12/2012 | Hong |
| 8,653,104 | B2 | 2/2014 | Hong |
| 9,737,524 | B2 | 8/2017 | Ihara et al. |
| 2006/0154963 | A1 | 7/2006 | Hong |
| 2010/0113515 | A1 | 5/2010 | Hong |
| 2010/0298375 | A1 | 11/2010 | Arai |
| 2013/0065921 | A1 | 3/2013 | Hong |
| 2015/0152084 | A1 | 6/2015 | Ihara et al. |
| 2016/0008348 | A1 | 1/2016 | Ihara et al. |

FOREIGN PATENT DOCUMENTS

| | | |
|---|---|---|
| CN | 101754758 A | 6/2010 |
| JP | 2006-518732 A | 8/2006 |
| KR | 10-2012-0010800 A | 2/2012 |
| WO | WO 2008/038849 A1 | 4/2008 |
| WO | WO 2009/153009 A1 | 12/2009 |
| WO | WO 2013/187075 A1 | 12/2013 |

OTHER PUBLICATIONS

Takashima et al, "Amyloid-B, Tau, and Dementia," Journal of Alzheimer's Disease 17 (2009) 729-736 729; (Year: 2009).*
Park et al. "Protective effect of the phosphodiesterase III inhibitor cilostazol on amyloid β-induced cognitive deficits associated with decreased amyloid β accumulation," Biochemical and Biophysical Research Communications 408 (2011) 602-608; (Year: 2011).*
Sato et al. "Structure-Activity Relationship for (+)-Taxifolin Isolated from Silymarin as an Inhibitor of Amyloid β Aggregation," Biosci. Biotechnol. Biochem., 77 (5), 1100-1103, 2013 (Year: 2013).*
Ihara et al. "Cilostazol Add-On Therapy in Patients with Mild Dementia Receiving Donepezil: A Retrospective Study," PLoS ONE 9(2): e89516, 2014. (Year: 2014).*
Agrawal et al., "Antidepressant Activity of Cilostazol: An Experimental Study," World Journal of Pharmaceutical Research, 4(2): 833-841 (2015).
Hiramatsu et al., "Cilostazol prevents amyloid ß peptide25-35-induced memory impairment and oxidative stress in mice," Br. J. Pharmacol., 161(8): 1899-1912 (2010).
Kim et al., "Anti-depressant effects of phosphodiesterase 3 inhibitor cilostazol in chronic mild stress-treated mice after ischemic stroke," Psychopharmacology (Berl.), 233(6): 1055-1066 (2016).
Maki et al., "Phosphodiesterase III inhibitor promotes drainage of cerebrovascular β-amyloid," Ann. Clin. Transl. Neurol., 1(8): 519-533 (2014).
Park et al., "Protective effect of the phosphodiesterase III inhibitor cilostazol on amyloid β-induced cognitive deficits associated with decreased amyloid β accumulation," Biochem. Biophys. Res. Commun., 408(4): 602-608 (2011).
Park et al., "Concurrent Treatment with Taxifolin and Cilostazol on the Lowering of β-Amyloid Accumulation and Neurotoxicity via the Suppression of P-JAK2/P-STAT3/NF-κB/BACE1 Signaling Pathways," PLoS One, 11(12): e0168286 (2016).
Sato et al., "Site-specific Inhibitory Mechanism for Amyloid B42 Aggregation by Catechol-type Flavonoids Targeting the Lys Residues," J. Biol. Chem., 288(32): 23212-23224 (2013).
Yoneyama et al., "Beneficial Effect of Cilostazol-Mediated Neuronal Repair Following Trimethyltin-Induced Neuronal Loss in the Dentate Gyrus," J. Neuroscience Res., 93: 56-66 (2015).
Japanese Patent Office, International Search Report in International Patent Application No. PCT/JP2017/017195 (dated Jun. 20, 2017).

* cited by examiner

*Primary Examiner* — Jeffrey S Lundgren
*Assistant Examiner* — Michael J Schmitt
(74) *Attorney, Agent, or Firm* — Leydig, Voit & Mayer, Ltd.

(57) ABSTRACT

Provided is a drug superior for preventing and/or treating dementia. It contains a carbostyril derivative of the following formula (1) (wherein R is a cycloalkyl group, A is a lower alkyl group, and a single bond or a double bond is present between the 3-position and the 4-position of the carbostyril nucleus) and dihydroquercetin.

9 Claims, 5 Drawing Sheets

(A)

(B)

white color area: Zone 1
horizontal line area: Zone 2
vertical line area: Zone 3
oblique line area: Zone 4 platform (A)

(B)

(C)

DRUG FOR PREVENTING AND/OR TREATING DEMENTIA

CROSS-REFERENCE TO RELATED APPLICATIONS

This patent application is a divisional of copending U.S. patent application Ser. No. 16/302,097, filed on Nov. 15, 2018, which is the U.S. national phase of International Patent Application No. PCT/JP2017/017195, filed May 1, 2017, which claims the benefit of Japanese Patent Application No. 2016-100092, filed on May 19, 2016, which are incorporated by reference in their entireties herein.

TECHNICAL FIELD

The present invention relates to a drug for preventing and/or treating dementia.

BACKGROUND ART

Dementia refers to a state in which organic change of the brain decreases memory function and other cognitive functions to the extent that the daily life is hindered. The main causative disease of dementia includes Alzheimer-type dementia and vascular dementia. Dementia includes core symptoms such as memory disorders, disorientation, dysexecutive function, agraphia, acalculia and the like, and behavioral and psychological symptoms of dementia (BPSD) such as anxiety, insomnia, increased aggression, depression, and disorders of wandering, delirium and the like.

Memory disorders and disorientation in human dementia patients correspond to spatial memory disorders in dementia animal model. The spatial memory means the ability to grasp and memorize the state and relationship that an object occupies in a three-dimensional space, such as the position, direction, posture, size, shape, spacing and the like of the object, and the spatial memory disorder means disorder of such spatial memory. The dysexecutive function is also called a disorder of working memory. The working memory means the ability to keep information in mind for a short time and simultaneously process same, and the working memory disorder means disorder of such working memory.

Prevention and treatment of dementia is important not only for improving QOL of patients but also reducing the burden of family members in nursing care and reducing health care costs. Major causative disease of dementia includes Alzheimer-type dementia accompanying intracerebral amyloid plaque and vascular dementia caused by cerebrovascular disease. In particular, the former has attracted attention as a disease occupying nearly half of all patients with dementia.

In recent years, it has been suggested that vascular pathology is also deeply involved in the pathology formation of Alzheimer's disease, and an approach from cardiovascular side is also being sought in the treatment of Alzheimer-type dementia.

One example thereof is cilostazol. Cilostazol is an antiplatelet drug used for secondary prevention after cerebral infarction such as lacunar infarction and the like, and recently, the following actions thereof are also attracting attention. That is, it has been reported that administration of cilostazol shows actions that (i) intracerebral accumulation of amyloid beta (hereinafter sometimes abbreviated as A$\beta$) is suppressed (non-patent documents 1, 2), (ii) reduction of cognitive function is suppressed (non-patent documents 1, 2), and (iii) cerebral blood flow in the vertebral artery, internal carotid artery, cerebral cortex, hypothalamus and the like increases (cilostazol package insert). Particularly, (i) is said to be related to the activation of cerebrovascular perivascular drainage pathway (brain interstitial flow), which is a waste discharge system in the brain.

It is highly likely that the cerebrovascular perivascular drainage pathway is a universal elimination pathway for not only A$\beta$ but also neurotoxic substances such as tau protein, $\alpha$-synuclein protein and the like. Administration of cilostazol is expected to be effective for various cognitive disorders (e.g., Alzheimer-type dementia, frontotemporal lobar degeneration, Lewy body dementia etc.) caused by accumulation of many neurotoxic proteins. Also, cerebral blood flow decrease/cerebrovascular disorder is a factor that promotes the onset and progress of dementia. In this regard, administration of cilostazol has a positive effect on both the improvement of cerebral blood flow and the prevention of cerebral infarction.

Non-patent document 3 describes that, as a result of administration of a cilostazol-containing feed to APP-SwDI transgenic mice, an alternation response in the Y-maze test increased in APP-SwDI transgenic mice administered with cilostazol as compared to the APP-SwDI transgenic mouse administered with a control feed, and it is suggested that cilostazol is beneficial for improving working memory disorder in dementia.

DOCUMENT LIST

Non-Patent Documents

Non-patent document 1: Park S H, et al. Protective effect of the phosphodiesterase III inhibitor cilostazol on amyloid $\beta$-induced cognitive deficits associated with decreased amyloid $\beta$ accumulation. Biochem Biophys Res Commun 2011; 408:602-608.

Non-patent document 2: Hiramatsu M, et al. Cilostazol prevents amyloid $\beta$ peptide(25-35)-induced memory impairment and oxidative stress in mice. Br J Pharmacol 2010 161:1899-1912.

Non-patent document 3: Masafumi Ihara, et al. Phosphodiesterase III inhibitor promotes drainage of cerebrovascular b-amyloid, Annals of Clinical and Translational Neurology, 2014.

SUMMARY OF THE INVENTION

Problems to be Solved by the Invention

The present invention aims to further improve the effect of a drug comprising cilostazol for preventing and/or treating dementia. Specifically, it aims to provide a drug effective not only for the core symptoms but also BPSD and effective even when the symptoms have progressed.

Means of Solving the Problems

The drug for preventing and/or treating dementia of the present invention characteristically contains a carbostyril derivative represented by the following formula (1) (wherein R is a cycloalkyl group, A is a lower alkyl group, and a single bond or a double bond is present between the 3-position and the 4-position of the carbostyril nucleus) or a salt thereof, and

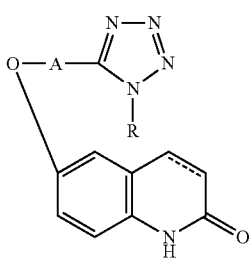

(1)

dihydroquercetin or a salt thereof.

Also, the drug for preventing and/or treating dementia of the present invention is characterized in that the active ingredient, a carbostyril derivative of the following formula (1) (wherein R is a cycloalkyl group, A is a lower alkyl group, and a single bond or a double bond is present between the 3-position and the 4-position of the carbostyril nucleus) or a salt thereof, and

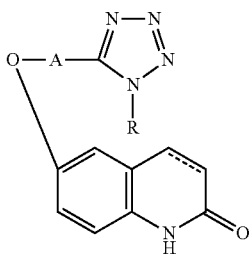

(1)

the active ingredient, dihydroquercetin or a salt thereof, are administered in combination.

Effect of the Invention

According to the present invention, a further effect for the prophylaxis and/or treatment of dementia is obtained than a single treatment of cilostazol.

DESCRIPTION OF EMBODIMENTS

Figure 1:
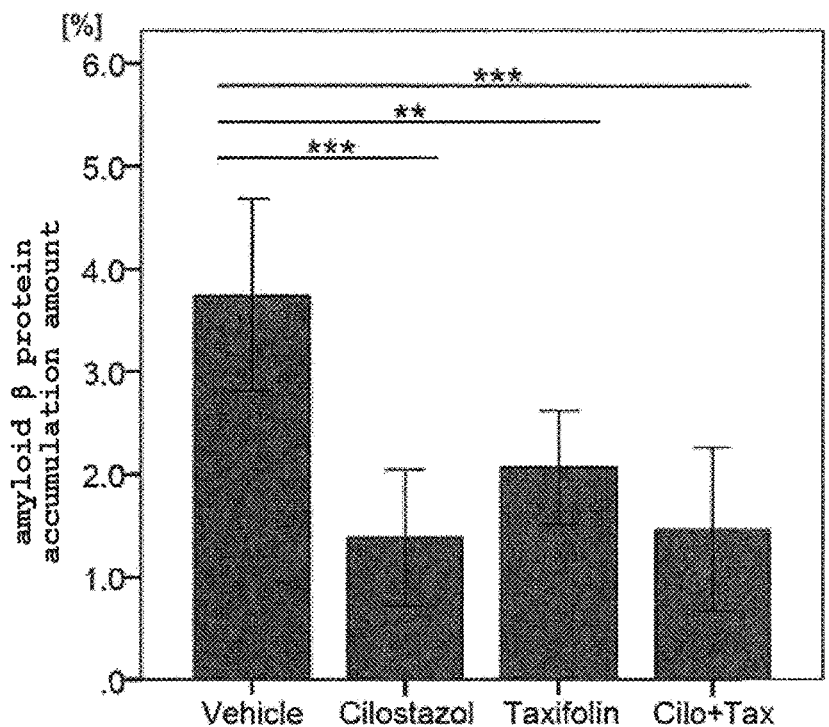
FIG. 1 shows amounts of Aβ deposition on the cerebral vessel wall of the mice of each group.

The embodiments of the present invention are described in detail below by reference to the accompanying drawings.

The embodiments are intended for facilitating understanding of the principle of the present invention. The scope of the present invention is not limited to the below-mentioned embodiments and other embodiments which are the following embodiments except that the constitutions thereof have been appropriately replaced by those skilled in the art are also included in the scope of the present invention.

The drug for preventing and/or treating dementia of the present embodiment contains a carbostyril derivative represented by the following formula (1) (wherein R is a cycloalkyl group, A is a lower alkyl group, and a single bond or a double bond is present between the 3-position and the 4-position of the carbostyril nucleus) or a salt thereof, and

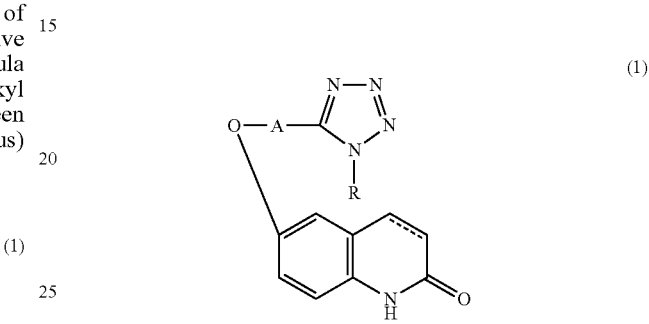

(1)

dihydroquercetin or a salt thereof.

In the drug for preventing and/or treating dementia of the present embodiment, the active ingredient of a carbostyril derivative represented by the following formula (1) (wherein R is a cycloalkyl group, A is a lower alkyl group, and a single bond or a double bond is present between the 3-position and the 4-position of the carbostyril nucleus) or a salt thereof, and

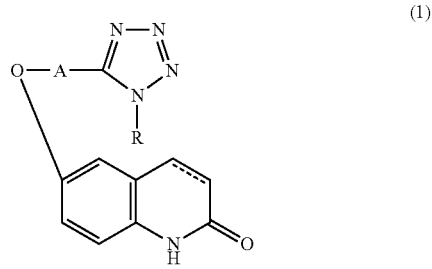

(1)

the active ingredient of dihydroquercetin or a salt thereof are administered in combination.

In the above-mentioned formula (1), the cycloalkyl group includes, for example, $C_3$-$C_8$ cycloalkyl groups such as cyclopropyl, cyclobutyl, cyclopentyl, cyclohexyl, cycloheptyl and cyclooctyl. Preferred cycloalkyl group is cyclohexyl.

In the above-mentioned formula (1), the lower alkyl group includes, for example, $C_1$-$C_6$ alkylene groups such as methylene, ethylene, propylene, tetramethylene, butylene and pentylene, with preference given to tetramethylene.

The drug of the present embodiment is used for preventing and/or treating dementia. In the present specification, "preventing" includes suppressing and delaying the onset of a disease, and includes not only prevention before developing a disease but also prevention of recurrence of a disease after treatment. On the other hand, "treatment" includes curing a symptom, improving a symptom and suppressing progress of a symptom. Dementia is not particularly limited and includes, for example, Alzheimer-type dementia, Lewy body dementia, frontotemporal dementia, cerebrovascular dementia, Parkinson's disease, Down's syndrome, Huntington's disease and the like.

The drug of the present embodiment is used for preventing and/or treating dementia and can prevent and/or treat not only core symptoms of dementia but also BPSD caused by core symptoms. BPSD emerge frequently as dementia progresses from moderate to severe. BPSD include aggressive behavior, delusion, sleep disorder, wandering, resistance to nursing care, falling due to hyperactivity, suffocation by impulsive food stealing and the like.

The drug of the present embodiment contains a carbostyril derivative or a salt thereof, and dihydroquercetin or a salt thereof. It also includes a form of simultaneously or separately, or sequentially administering a combination of these. For example, a tablet or fine granule containing a carbostyril derivative as an active ingredient, and a tablet or fine granule containing dihydroquercetin as an active ingredient are combined, and the drug of the present embodiment also encompasses sequential administration of these.

In other words, the "drug containing a carbostyril derivative or a salt thereof, and dihydroquercetin or a salt thereof" is, for example, as follows.

A form for simultaneous or separate, or sequential administration of the active ingredient carbostyril derivative or a salt thereof and the active ingredient dihydroquercetin or a salt thereof.

A form containing the active ingredient carbostyril derivative or a salt thereof and the active ingredient dihydroquercetin or a salt thereof.

A preferable carbostyril derivative is 6-[4-(1-cyclohexyl-1H-tetrazol-5-yl)butoxy]-3,4-dihydrocarbostyril represented by the following formula (2), which is placed on the market under the trade name of cilostazol as an anti-platelet drug.

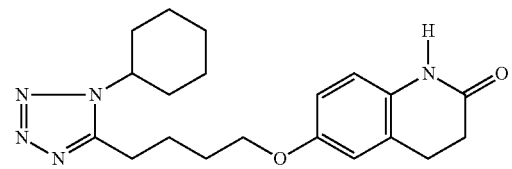

(2)

While the average particle size of cilostazol is not particularly limited, it is preferably, for example, 10 μm-2000 μm. When the average particle size is larger than 2000 μm, an expensive equipment is required for preparing resin particles. When the average particle size is smaller than 10 μm, absorption in the lower gastrointestinal tract may be poor.

A salt of a carbostyril derivative can be easily formed by reacting with a pharmaceutically acceptable acid. Examples of the acid include inorganic acids such as hydrochloric acid, sulfuric acid, phosphoric acid, hydrobromic acid and the like, and organic acids such as oxalic acid, maleic acid, fumaric acid, malic acid, tartaric acid, citric acid, benzoic acid and the like.

Carbostyril derivative and a salt thereof, and a production method thereof are disclosed in JP-A-55-35019 (corresponding U.S. Pat. No. 4,277,479).

Dihydroquercetin is a compound represented by the following formula (3).

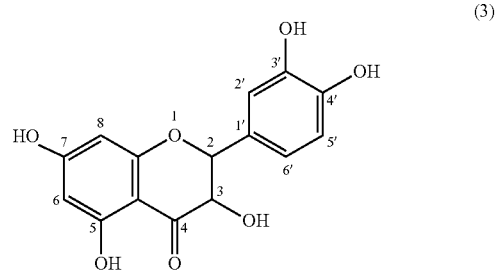 [SMILES: O=C1c2c(O)cc(O)cc2OC(c2ccc(O)c(O)c2)C1O]

(3)

Dihydroquercetin contains 4 kinds of stereoisomers due to the steric configurations of the 2-position and the 3-position. A compound represented by the following formula (4), which is one kind thereof, is called taxifolin.

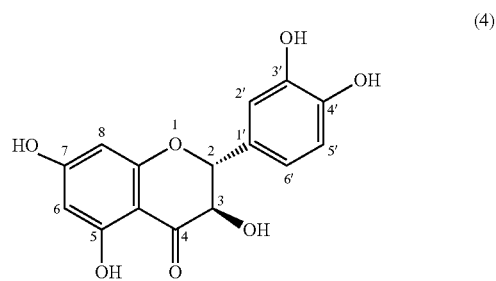 [SMILES: O=C1c2c(O)cc(O)cc2O[C@H](c2ccc(O)c(O)c2)[C@H]1O]

(4)

Dihydroquercetin also encompasses a dihydroquercetin derivative. As the dihydroquercetin derivative, for example, a glycoside in which sugar is bonded to at least one hydroxyl group at the 3, 3', 4', 5 or 7-position of dihydroquercetin can be mentioned.

A salt of dihydroquercetin can be formed easily by reacting with a pharmaceutically acceptable acid. Examples of such salts include alkali metal salts such as sodium salt, potassium salt and the like.

Dihydroquercetin or a salt thereof can be produced by, for example, chemical synthesis or extraction from Siberian larch.

While the mixing ratio of the carbostyril derivative and dihydroquercetin is not particularly limited, it can be set to, for example, 1:5-1:20 in weight ratio.

The dose of the active ingredient in the drug of the present embodiment can be appropriately determined according to the age, sex, body weight, symptom and the like of the patient. For example, 35-400 mg, preferably 100-200 mg, of a carbostyril derivative per day, and 150-2000 mg, preferably 500-1000 mg, of dihydroquercetin per day can be administered to an adult (body weight 50 kg) at once or in two to several divided portions.

The administration method of the drug of the present embodiment is not particularly limited and, for example, a carbostyril derivative and dihydroquercetin can be administered in combination simultaneously or separately, or sequentially with a time difference of several hours to several days. For sequential administration, either component may be administered first.

The drug of the present embodiment can be prepared into, for example, a preparation for oral administration such as tablet, granule, fine granule, capsule and the like, various liquid preparations suitable for oral administration, or a preparation for parenteral administration such as injection and suppository.

A preparation for oral administration can be obtained by formulating a fine powder of the drug of the present embodiment, a dispersing agent and/or a dissolution improving agent together with a pharmaceutical carrier in the form of tablet, granule, fine granule, capsule or the like. Dispersibility and/or dissolution absorbability of the fine powder of the carbostyril derivative can be enhanced by adding a dispersing agent and/or dissolution improving agent.

As the pharmaceutical carrier, excipient, binder, disintegrant, lubricant, plasticizer and the like can be used. As the excipient, for example, sucrose, sodium chloride, mannitol, lactose, glucose, starch, calcium carbonate, kaolin, crystalline cellulose, low-substituted hydroxypropylcellulose, hydroxypropylmethylcellulose acetate succinate, silicate and the like can be used. As the binder, for example, water, ethanol, propanol, glucose solution, starch solution, gelatin solution, sodium carboxymethylcellulose, methylcellulose, hydroxypropylcellulose, hydroxypropylmethylcellulose, poly(vinyl alcohol), polyvinylpyrrolidone and the like can be used. As the disintegrant, for example, calcium carboxymethylcellulose, dry starch, sodium hydrogen carbonate, calcium carbonate, polyoxyethylene sorbitan fatty acid esters, stearic acid monoglyceride, starch, sodium carboxymethyl starch, croscarmellose sodium and the like can be used. As the lubricant, for example, purified talc, stearate salt, boric acid powder, polyethylene glycol, colloidal silicic acid, hydrogenated oil and the like can be used. As the plasticizer, for example, glycerol fatty acid ester, dioctylphthalate, dibutylphthalate, triacetin, triethyl citrate, castor oil and the like can be used.

As the dispersing agent and/or dissolution improving agent, water-soluble polymer, surfactant and the like can be used. As the water-soluble polymer, for example, hydroxypropylcellulose, poly(vinyl alcohol), polyvinylpyrrolidone, hydroxypropylmethylcellulose, carboxymethylcellulose, polyacrylic acid and the like can be used. As the surfactant, for example, alkylsulfate such as sodium lauryl sulfate, magnesium lauryl sulfate and the like; polyglycerol fatty acid ester such as decaglycerylmonolaurate, decaglycerylmonomyristate and the like; polyoxyethylene sorbitan fatty acid ester such as polyoxyethylene sorbitan monooleate and the like; polyethylene glycol fatty acid ester such as polyoxyethylene monostearate and the like; polyoxyethylene alkyl ether such as polyoxyethylene lauryl ether and the like; polyoxyethylene castor oil such as polyoxyethylene hydrogenated castor oil and the like, and hydrogenated castor oil; sucrose fatty acid ester such as sucrose stearate, sucrose palmitate and the like, and the like can be used.

It is preferable to blend 0.001-100 parts by weight, preferably 0.01-10 parts by weight, of a dispersing agent and/or a dissolution improving agent per 1 part by weight of a fine powder of the drug of the present embodiment. When the amount of the dispersing agent and/or dissolution improving agent to be added is less than 0.001 part by weight, absorption becomes poor. On the other hand, when the amount to be added is higher than 100 parts by weight, the powder may be subject to toxicity such as mucosal damage and restriction by the Pharmaceutical Affairs Law.

To prepare a tablet, the drug of the present embodiment and the above-mentioned preparation carrier are tableted by a conventional method. Granule or fine granule can be prepared by adding the above-mentioned preparation carrier to a fine powder of the drug of the present embodiment, and granulating by fluidized bed granulation, high-speed stirring granulation, agitation fluidized bed granulating, centrifugal fluidizing granulation, extrusion-granulation and the like. A capsule is prepared by mixing with an inactive pharmaceutical filler or diluent and packed in a hard gelatin capsule or soft capsule.

The average particle size of the drug of the present embodiment can be adjusted by using, for example, hammer mill, jet mill, rotary ball mill, vibrating ball mill, shaker mill, rod mill, tube mill and the like.

In the drug of the present embodiment, tablet, granule and fine granule can also be coated with a sustained-release coating base. As the sustained-release coating base, cellulose acetate phthalate, hydroxypropylmethylcellulose phthalate, methacrylic acid copolymer, ethylcellulose and the like can be used. This makes it possible to provide, for example, a dissolution ability of the drug in the lower gastrointestinal tract.

An oral liquid preparation is prepared by mixing the drug of the present embodiment, and sweetener (e.g., sucrose), preservative (e.g., methylparaben, propylparaben), colorant, flavor and the like.

Among the preparations for parenteral administration, an injection preparation is prepared in the form of, for example, liquid, emulsion or suspension, and is isotonic to blood. A preparation in the form of liquid, emulsion or suspension is prepared by using, for example, aqueous medium, ethyl alcohol, propylene glycol, ethoxylated isostearyl alcohol, polyoxylated isostearyl alcohol, polyoxyethylene sorbitan fatty acid ester. As the aqueous medium, water or a water-containing medium can be mentioned. As water, sterile water is used. Examples of the water-containing medium include saline, PBS (phosphate buffered saline), lactated Ringer's solution and the like.

In injection preparation, additives generally used in the technical field can be appropriately used. Examples of the additive include isotonicity agent, stabilizer, buffering agent, preservative, chelating agent, antioxidant, solubilizing agents and the like. Examples of the isotonicity agent include saccharides such as glucose, sorbitol, mannitol and the like, sodium chloride, glycerol, propylene glycol, polyethylene glycol and the like. Examples of the stabilizer include sodium sulfite and the like. Examples of the buffering agent include borate buffering agent, phosphate buffering agent, citrate buffering agent, tartrate buffering agent, acetate buffering agent and the like. Examples of the preservative include paraoxybenzoate, benzyl alcohol, chlorocresol, phenethyl alcohol, benzethonium chloride and the like. Examples of the chelating agent include sodium edetate, sodium citrate and the like. Examples of the antioxidant include sodium sulfite, sodium bisulfite, sodium ascorbate, sodium thiosulfate and the like. Examples of the solubilizing agent include dextran, polyvinylpyrrolidone, sodium benzoate, ethylenediamine, salicylamide, nicotinamide, polyoxyethylene hydrogenated castor oil derivative and the like.

An injection preparation may contain a pH adjuster. The pH adjuster may be acids or bases. Specifically, examples of the acids include ascorbic acid, hydrochloric acid, gluconic acid, acetic acid, lactic acid, boric acid, phosphoric acid, sulfuric acid, tartaric acid, citric acid and the like. Examples of the bases include potassium hydroxide, calcium hydroxide, sodium hydroxide, magnesium hydroxide, monoethanolamine, diethanolamine, triethanolamine and the like.

The drug of the present embodiment can be applied to human as well as, for example, mammal other than human such as monkey, bovine, horse, swine, sheep, dog, cat, rat, mouse and the like.

The drug of the present embodiment has a remarkable effect exerted by a combination of a carbostyril derivative and dihydroquercetin. That is, as shown in the below-mentioned examples, cilostazol is effective for maintaining working memory but sometimes ineffective for maintaining spatial memory. However, the combined use of taxifolin renders cilostazol also effective for maintaining spatial memory. On the other hand, single administration of taxifolin sometimes develops an excitatory action (fighting etc.). Combined use of cilostazol sedates excitement. That is, it can effectively prevent onset of BPSD difficult to avoid by single administration of taxifolin, or a suppressive action and improving effect on the BPSD after the onset can be expected. Antipsychotic agents, mood stabilizers, anti-anxiety drugs, sleep inducing drugs and the like are sometimes used for dementia patients to suppress their BPSD. The drug of the present embodiment can accurately suppress BPSD, and the kind and amount of pharmaceutical products taken by patients can be expected to be reduced.

Thus, the drug of the present embodiment is effective for not only the core symptoms of dementia represented by memory disorders but also BPSD such as increased aggressiveness, anxiety and the like, and is extremely effective for the treatment of dementia.

EXAMPLES

1. Immunohistochemistry

Analysis was performed by using 8-month-old APP-SwDI transgenic mice administered with a normal feed (n=5), APP-SwDI transgenic mice administered with a cilostazol-containing feed (n=5), APP-SwDI transgenic mice administered with a taxifolin-containing feed (n=6), and APP-SwDI transgenic mice administered with a feed containing cilostazol and taxifolin (feed containing the drug of this Example) (n=6), totaling 22 mice. The cilostazol-containing feed, the taxifolin-containing feed, and the feed containing cilostazol and taxifolin were administered from 4-week-old to 8-month-old. The concentration of cilostazol in the cilostazol-containing feed was 0.3 wt %, and the concentration of taxifolin in the taxifolin-containing feed was 3 wt %. The concentration of cilostazol and the concentration of taxifolin in the feed containing cilostazol and taxifolin were respectively 0.3 wt % and 3 wt %. All the APP-SwDI transgenic mice used were homozygous male mice. The 4-week-old APP-SwDI transgenic mice are considered to be in the initial stage of accumulation of Aβ in the brain blood vessel, i.e., the initial stage of cerebral amyloid angiopathy, and neuronal loss is considered to be not progressing much in this stage.

The brain of an 8-month-old APP-SwDI transgenic mice was perfusion fixed using 4% para-formaldehyde, the removed brain was dehydration-treated for a whole day. A paraffin block of the fixed brain tissue was prepared, and the paraffin block was sliced in 6 microns by microtome. Aβ deposition on the blood vessel wall was observed under a microscope by immunohistochemistry method for Aβ. The hippocampus region was traced in a section which was cut 1 mm outside the midline, and the percentage of the Aβ accumulation area in the region of interest was measured by using image analysis software ImageJ (National Institutes of Health. USA).

FIG. 1 shows mean of the amount of Aβ deposition in each group of the mice. Error bars show standard deviation.

The APP-SwDI transgenic mice administered with a cilostazol-containing feed, APP-SwDI transgenic mice administered with a taxifolin-containing feed, and APP-SwDI transgenic mice administered with a feed containing cilostazol and taxifolin showed a significant decrease in the intracerebral Aβ accumulation amount compared to the APP-SwDI transgenic mice administered with a normal feed.

2. Carbon Dioxide Gas Inhalation Test

Analysis was performed by using 12-month-old C57BL/6J mice administered with a normal feed (n=4), APP-SwDI transgenic mice administered with a normal feed (n=10), APP-SwDI transgenic mice administered with a cilostazol-containing feed (n=4), APP-SwDI transgenic mice administered with a taxifolin-containing feed (n=5), and APP-SwDI transgenic mice administered with a feed containing cilostazol and taxifolin (n=7), totaling 30 mice. The feeds containing cilostazol, taxifolin, or cilostazol and taxifolin were administered from 4-week-old to 12-month-old. The concentration of cilostazol in the cilostazol-containing feed was 0.3 wt % and the concentration of taxifolin in the taxifolin-containing feed was 3 wt %. All the APP-SwDI transgenic mice used were homozygous male mice.

The mice were anesthetized by intraperitoneal injection of α-chloralose and urethane. Then, endotracheal intubation was performed and the baseline of the cerebral blood flow was measured. Thereafter, 5% $CO_2$ was supplied, and the cerebral blood flow was sequentially measured for 5 min. Relative increase rate was measured from the changes in the cerebral blood flow between the baseline and after 5% $CO_2$ supply. The cerebral blood flow was measured by a laser speckle blood flow imager (OZ-2, OMEGAWAVE, INC.).

Figure 2:
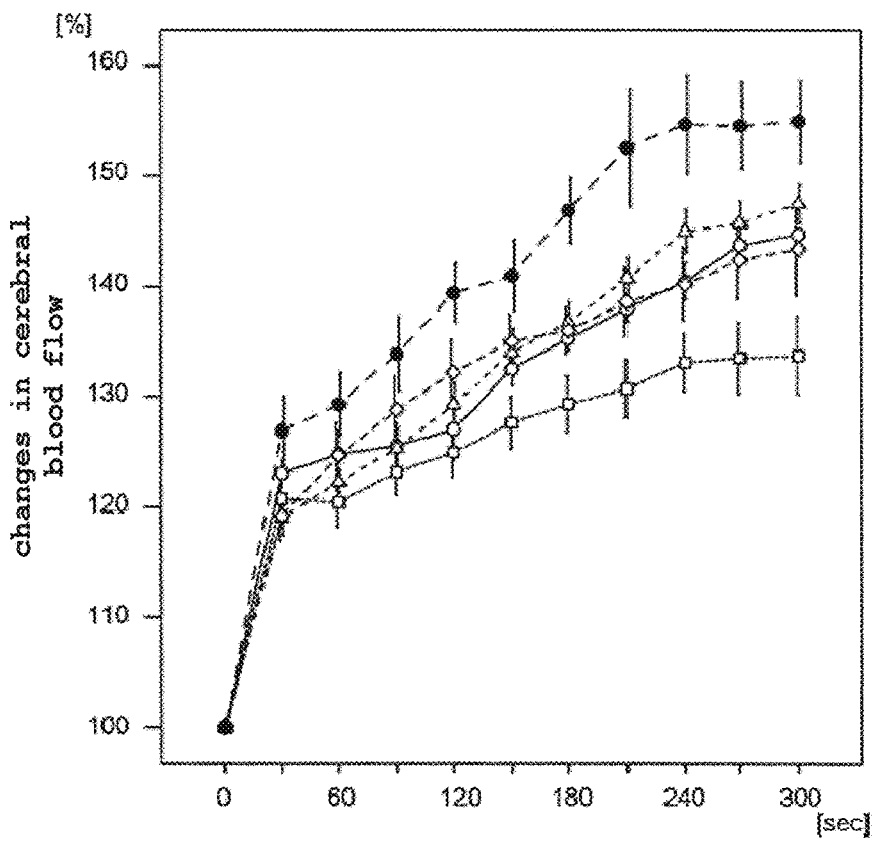
FIG. 2 shows mean of relative increase rate of the cerebral blood flow after supply of 5% $CO_2$ in the mice of each group.

FIG. 2 is a graph showing mean of relative increase rate of the cerebral blood flow after supply of 5% $CO_2$ in the mice of each group. The horizontal axis shows time (sec) after start of 5% $CO_2$ supply. The open circle group shows C57BL/6J mice administered with a normal feed, the square group shows APP-SwDI transgenic mice administered with a normal feed, the triangle group shows APP-SwDI transgenic mice administered with a cilostazol-containing feed, the rhombus group shows APP-SwDI transgenic mice administered with a taxifolin-containing feed, and the black circle group shows APP-SwDI transgenic mice administrated with a feed containing cilostazol and taxifolin. Error bars show standard error.

In the APP-SwDI transgenic mice administered with a normal feed, the increase rate of the cerebral blood flow decreased after 5% $CO_2$ supply as compared to the C57BL/6J mice. In the APP-SwDI transgenic mice administrated with a cilostazol-containing feed and the APP-SwDI transgenic mice administered with a taxifolin-containing feed, the cerebral blood flow increase rate increased as compared to the APP-SwDI transgenic mice administered with a normal feed. In the APP-SwDI transgenic mice administrated with a taxifolin-containing feed, the cerebral blood flow increase rate rapidly increased after 5% $CO_2$ supply, whereas in the APP-SwDI transgenic mice administered with a cilostazol-containing feed, the cerebral blood flow increase rate increased after a certain period of time after 5% $CO_2$ supply. These results show that taxifolin and cilostazol improved abnormality in the blood vessel reactivity of the APP-SwDI transgenic mice by mechanisms different from each other. However, according to repeated measurement and variance analysis, a significant difference was absent between the APP-SwDI transgenic mice administrated with a normal feed group and the taxifolin administration group and cilostazol administration group, and a significant difference was confirmed only between the group of APP-SwDI transgenic mice administrated with a normal feed and the group of APP-SwDI transgenic mice administrated with a feed containing cilostazol and taxifolin group (p<0.001). It was suggested that combined use of drugs having different action mechanisms of pharmacological effects enhances a treatment effect on dementia by the expression of the action of each drug.

3. Water Maze Test

A water maze test was performed by using 8-month-old C57BL/6J mice (n=15), APP-SwDI transgenic mice administrated with a normal feed (n=17), APP-SwDI transgenic mice administrated with a cilostazol-containing feed (n=10), APP-SwDI transgenic mice administrated with a taxifolin-containing feed (n=10), and APP-SwDI transgenic mice administrated with a feed containing cilostazol and taxifolin (n=9), totaling 61 mice. The cilostazol-containing feed, the taxifolin-containing feed, and the feed containing cilostazol and taxifolin were administered from 4-week-old to 8-month-old. The concentration of cilostazol in the cilostazol-containing feed was 0.3 wt %, and the concentration of taxifolin in the taxifolin-containing feed was 3 wt %. The concentration of cilostazol and the concentration of taxifolin in the feed containing cilostazol and taxifolin were respectively 0.3 wt % and 3 wt %. All the APP-SwDI transgenic mice used were homozygous male mice.

The water maze test is a test for evaluating the visuospatial cognitive ability of mouse by utilizing the habit of avoiding water and escaping therefrom. The water maze used in this experiment was Morris water maze manufactured by Brain Science Idea, having a circular pool of a water tank entirely painted black with inner diameter 120 cm, wall height 30 cm. One transparent acrylic circular platform for escape with diameter 10 cm, height 10 cm was set at 30 cm from the center of the pool and 30 cm from the periphery. Clues such as poster, photograph and the like were arranged on the wall so that the mice could memorize various spatial arrangements in the surroundings, and the locations of these clues were always unchanged during the experiment. The pool was filled with water to a depth of 11 cm, and a platform was installed at about 1 cm below the water surface as in FIG. 3(A).

Figure 3:
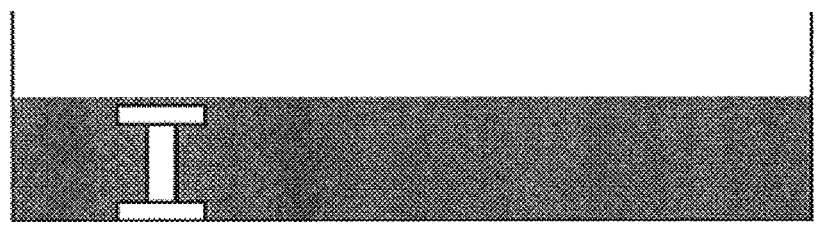
FIG. 3 shows an appearance of a circular pool used in a water maze test, wherein (A) is a cross sectional view and (B) is a top view.
Figure 3:
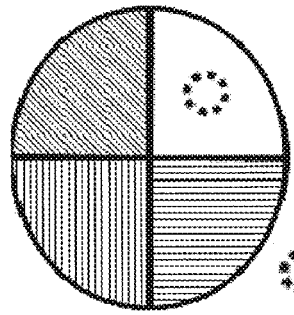

In all tests, Zone-2 in FIG. 3(B) was set as a start position. Zone-1 to Zone-4 show quadrant regions in the circular pool. The mice were gently placed on the water surface while facing the wall of the pool so that they could not see the location of the platform.

The tests were performed from the first day to the fourth day, 4 trials per day. In each trial, the total swimming distance and the time required for reaching the platform (swimming time) were measured. When the mouse failed to reach on the platform within 60 seconds, the experimenter kept the mouse on the platform for 15 seconds and finished the test, and 60 seconds was taken as the swimming time of the mouse.

On the fifth day, the mice were made to swim for 60 seconds with the platform removed from the pool (probe test). In the test, the residence time in Zone-1 where the goal was placed from the first day to the fourth day was measured.

Figure 4:
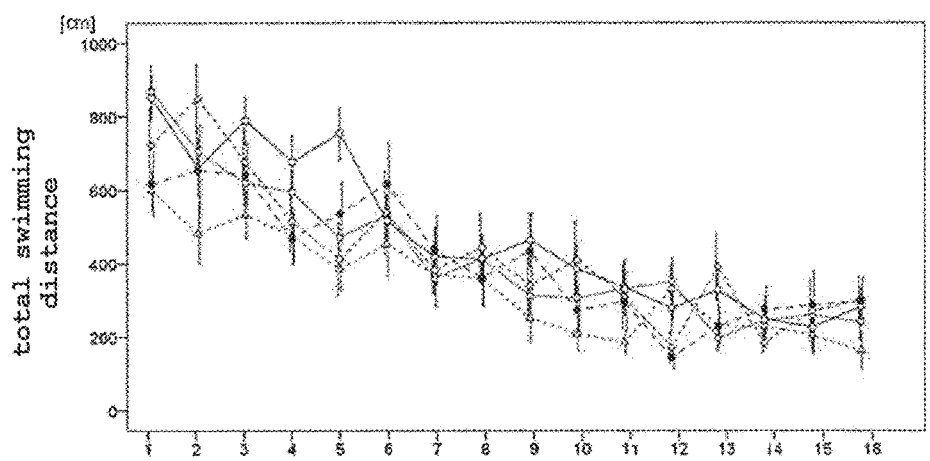
FIG. 4 shows the results of a water maze test, wherein (A) shows mean of the total swimming distance of the mice of each group, (B) shows mean of the swimming time of the mice of each group, and (C) shows mean of the residence time in Zone-1 of the mice of each group in the probe test.
Figure 4:
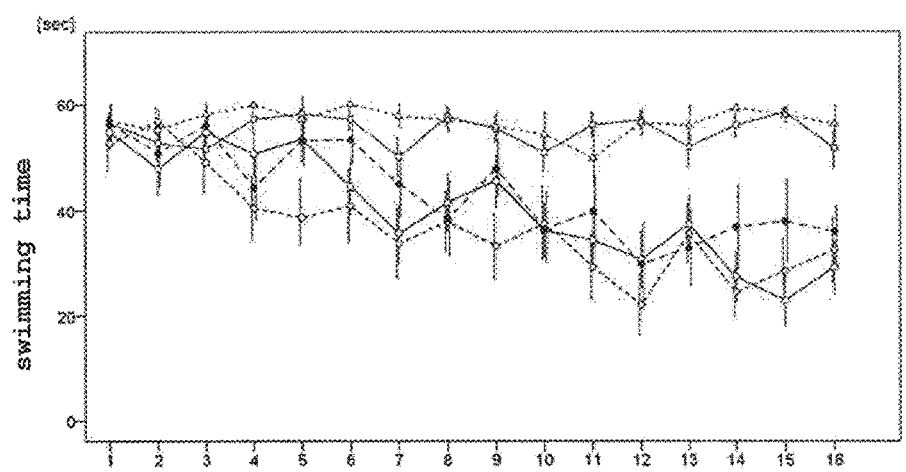
Figure 4:
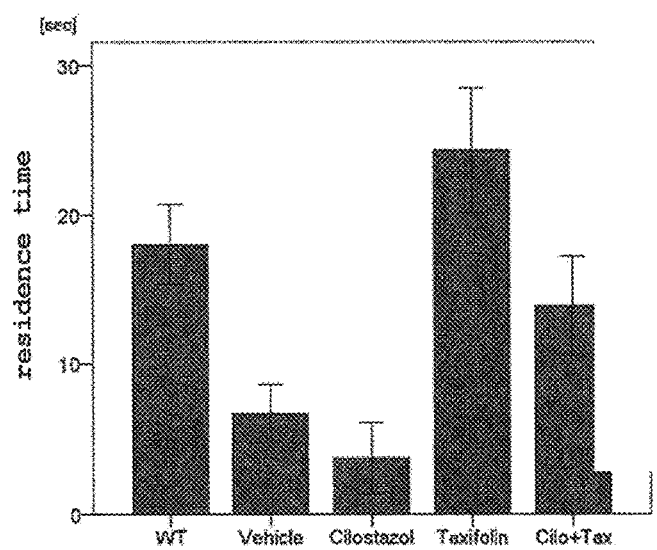

FIG. 4(A) shows mean of the total swimming distance of the mice of each group from the first day to the fourth day, and FIG. 4(B) shows mean of the time until the mice of each group reached the platform (swimming time) from the first day to the fourth day. The horizontal axis shows number of trials for both. The open circle group shows C57BL/6J mice administrated with a normal feed, the square group shows APP-SwDI transgenic mice administrated with a normal feed, the triangle group shows APP-SwDI transgenic mice administrated with a cilostazol-containing feed, the rhombus group shows APP-SwDI transgenic mice administrated with a taxifolin-containing feed, and the black circle group shows APP-SwDI transgenic mice administrated with a feed containing cilostazol and taxifolin. Error bars show standard error.

In the mice of 5 groups, the total swimming distances did not show a significant difference, thus indicating that a significant difference was absent in the motility function of the mice. On the other hand, in the swimming time to reach the goal, the C57BL/6J mice shortened the time to reach the platform in each trial, whereas the time was not shortened in the APP-SwDI transgenic mice administrated with a normal feed, and a disorder of visuospatial memory was suggested. This abnormality was the same as in the APP-SwDI transgenic mice administrated with a cilostazol-containing feed, and the visuospatial memory disorder improving effect of cilostazol was considered to be limited in the APP-SwDI transgenic mice. On the other hand, the APP-SwDI transgenic mice administrated with a taxifolin-containing feed and the APP-SwDI transgenic mice administrated with a feed containing cilostazol and taxifolin showed the same results as in the C57BL/6J mouse. This has revealed that the drug of this Example improves visuospatial memory disorder of the APP-SwDI transgenic mice. In addition, it was shown that taxifolin dramatically improves visuospatial memory disorder of APP-SwDI transgenic mice.

FIG. 4(C) shows mean (in seconds) of the residence time of the mice of each group in Zone-1 in a probe test in which the goal installed until then was removed. Error bars show standard error.

The residence time in Zone-1 where the goal was originally installed was short in the APP-SwDI transgenic mice administrated with a normal feed as compared to the C57BL/6J mice, and a disorder of visuospatial memory was suggested. This abnormality was the same as in the APP-SwDI transgenic mice administrated with a cilostazol-containing feed, and the visuospatial memory disorder improving effect of cilostazol was considered to be limited in the APP-SwDI transgenic mice. On the other hand, the APP-SwDI transgenic mice administrated with a taxifolin-containing feed and the APP-SwDI transgenic mice administrated with a feed containing cilostazol and taxifolin showed the same results as in the C57BL/6J mouse. This has revealed that cilostazol and taxifolin improve visuospatial memory disorder of the APP-SwDI transgenic mice.

4. Survival Curve

The APP-SwDI transgenic mice administrated with a normal feed (n=40), APP-SwDI transgenic mice administrated with a cilostazol-containing feed (n=65), APP-SwDI transgenic mice administrated with a taxifolin-containing feed (n=33), and APP-SwDI transgenic mice administrated with a feed containing cilostazol and taxifolin (n=33), which were born from Apr. 1, 2014 to Nov. 30, 2015, were used to plot and analyze a survival curve of the mice. The death of mice does not include slaughter accompanying implementation of the animal experiment.

Figure 5:
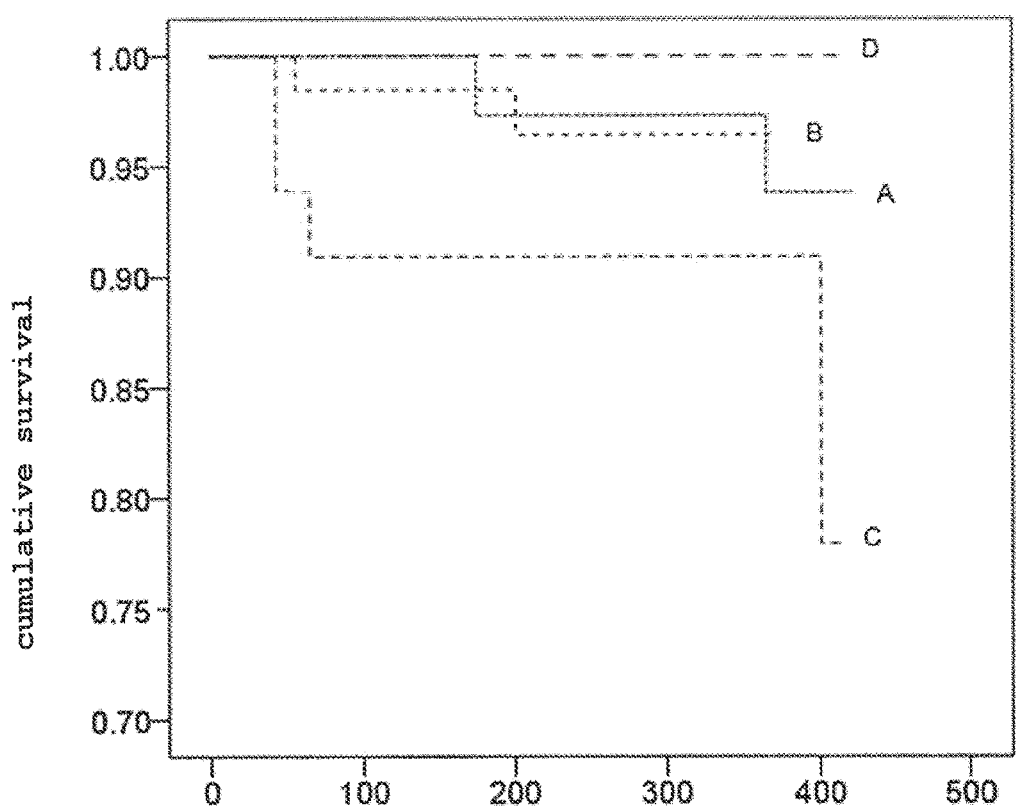
FIG. 5 shows a cumulative survival rate of the mice of each group.

FIG. 5 shows a cumulative survival rate of the mice of each group on the vertical axis and the number of days after birth on the horizontal axis.

A shows a group of APP-SwDI transgenic mice administrated with a normal feed, B shows a group of APP-SwDI transgenic mice administrated with a cilostazol-containing feed, C shows a group of APP-SwDI transgenic mice administrated with a taxifolin-containing feed group, and D shows a group of APP-SwDI transgenic mice administrated with a feed containing cilostazol and taxifolin.

Generally, the lifespan of a mouse is not less than two years, and it is comparatively rare that a mouse dies within 500 days under the observation at this time. However, the APP-SwDI transgenic mice administrated with a taxifolin-containing feed died clearly more than other mice. On the other hand, surprisingly, death of the mice was not seen in the APP-SwDI transgenic mice administrated with a feed containing cilostazol and taxifolin. This shows that the drug of this embodiment is also effective for the BPSD such as increased aggressiveness, anxiety and the like.

5. Hair Loss Score

Hair loss occurs when mice fight. Thus, the extent of hair loss of each mouse was described in 4 grades of Grade: 0-3 and taken as a hair loss score. Almost normal state is Grade: 0 and hair loss over nearly whole body is Grade: 3. Less than 50% of the whole body surface was classified as Grade: 1 and not less than 50% was classified as Grade: 2.

Analysis was performed by using 13-month-old C57BL/6J mice (n=5), APP-SwDI transgenic mice administrated with a normal feed (n=14), APP-SwDI transgenic mice administrated with a taxifolin-containing feed (n=4), APP-SwDI transgenic mice administrated with a feed containing cilostazol and taxifolin (n=12), totaling 35 mice. The information of mice was concealed and two evaluators independently evaluated the hair loss score. Mean of each evaluation was taken as the hair loss score of the mice.

Figure 6:
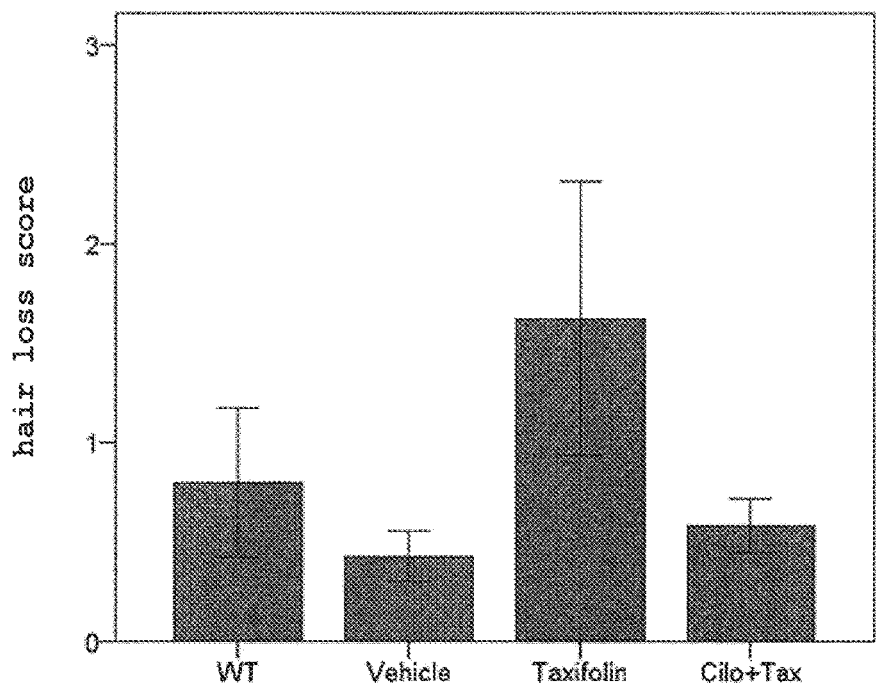
FIG. 6 shows mean of the hair loss score of the mice of each group.

FIG. 6 shows mean of the hair loss score of the mice of each group. Error bars show standard error.

A clearly severe hair loss was confirmed in the APP-SwDI transgenic mice administrated with a taxifolin-containing feed as compared to the APP-SwDI transgenic mice administrated with a normal feed. However, such tendency was not observed in the APP-SwDI transgenic mice administrated with a feed containing cilostazol and taxifolin, thus suggesting a decrease in fighting. This shows that the drug of this embodiment is also effective for the BPSD such as increased aggressiveness, anxiety and the like.

6. Y-Maze Test

Y-maze test was performed by using 13-month-old C57BL/6J mice (n=4), APP-SwDI transgenic mice administrated with a normal feed (n=14), APP-SwDI transgenic mice administrated with a taxifolin-containing feed (n=7), and APP-SwDI transgenic mice administrated with a feed containing cilostazol and taxifolin (n=14), totaling 39 mice. The cilostazol-containing feed, the taxifolin-containing feed, and the feed containing cilostazol and taxifolin were administered from 4-week-old to 13-month-old. The concentration of cilostazol in the cilostazol-containing feed was 0.3 wt %, and the concentration of taxifolin in the taxifolin-containing feed was 3 wt %. The concentration of cilostazol and the concentration of taxifolin in the feed containing cilostazol and taxifolin were respectively 0.3 wt % and 3 wt %. All the APP-SwDI transgenic mice used were homozygous male mice.

In the "APP-SwDI transgenic mice administrated with a feed containing cilostazol and taxifolin (n=3)", as mentioned above, the blood concentration of this mouse was measured after administration of the feed containing cilostazol and taxifolin. As a result, cilostazol (or metabolite of cilostazol) and taxifolin (or metabolite of taxifolin) were detected in the blood. Thus, the presence of cilostazol and taxifolin inside the body of this mouse was confirmed.

In the Y-maze test, according to the general practice method, the alternation response rate was measured from the results of the test for 8 minutes. An increase of this alternation response is considered to show superior working memory.

Figure 7:
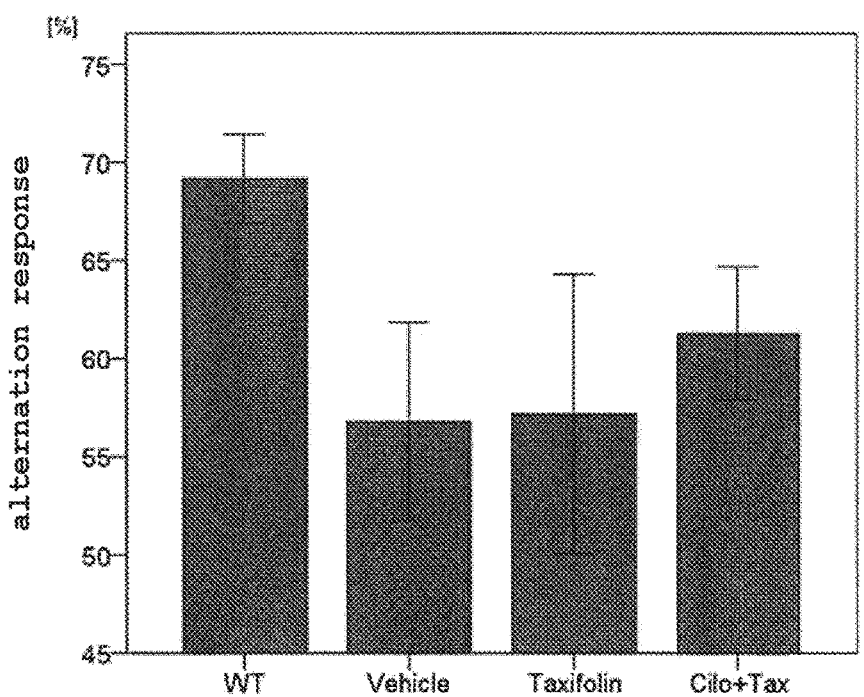
FIG. 7 shows the results of a Y-maze test.

FIG. 7 is a graph showing an average alternation response rate of the mice of each group. Error bars show standard error.

The alternation response rate decreased in the APP-SwDI transgenic mice as compared to the C57BL/6J mice, thus suggesting disorder of working memory. In the taxifolin administration mice, significant improvement was not observed, and APP-SwDI transgenic mice administrated with a feed containing cilostazol and taxifolin showed a tendency toward increase in the alternation response. It was therefore shown that combined use of cilostazol and taxifolin can improve disorder of working memory of APP-SwDI transgenic mice even in a fairy advanced stage of dementia.

INDUSTRIAL APPLICABILITY

It is utilizable for preventing and/or treating dementia.

The invention claimed is:

1. A method for improving memory disorders and behavioral and psychological symptoms of dementia (BPSD) in a patient with dementia comprising administering to the patient a combination of an effective amount of (a) a carbostyril derivative represented by formula (1)

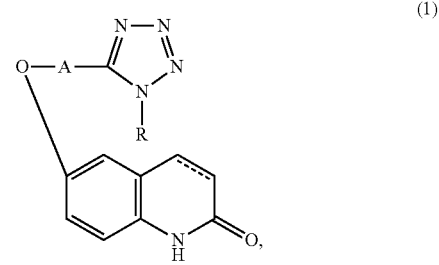

wherein R is a cycloalkyl group, A is a lower alkyl group, and a single bond or a double bond is present between the 3-position and the 4-position of the carbostyril nucleus, or a salt thereof, and (b) an effective amount of dihydroquercetin or a salt thereof.

2. The method according to claim 1, wherein the carbostyril derivative is 6-[4-(1-cyclohexyl-1H-tetrazol-5-yl) butoxy]-3,4-dihydrocarbostyril.

3. The method according to claim 1, wherein the dementia is Alzheimer-type dementia, Lewy body dementia, frontotemporal dementia, cerebrovascular dementia, Parkinson's disease, Down's syndrome, or Huntington's disease.

4. A method for improving spatial memory disorders in a patient with dementia comprising administering to the patient a combination of (a) an effective amount of a carbostyril derivative represented by formula (1)

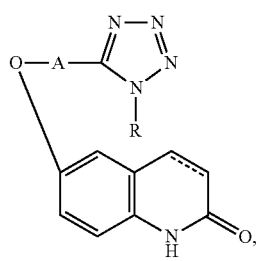

wherein R is a cycloalkyl group, A is a lower alkyl group, and a single bond or a double bond is present between the 3-position and the 4-position of the carbostyril nucleus, or a salt thereof, and (b) an effective amount of dihydroquercetin or a salt thereof.

5. The method according to claim 4, wherein the carbostyril derivative is 6-[4-(1-cyclohexyl-1H-tetrazol-5-yl)butoxy]-3,4-dihydrocarbostyril.

6. The method according to claim 4, wherein the dementia is Alzheimer-type dementia, Lewy body dementia, frontotemporal dementia, cerebrovascular dementia, Parkinson's disease, Down's syndrome, or Huntington's disease.

7. A method for suppressing excitatory action in a patient with dementia comprising administering to the patient a combination of (a) an effective amount of a carbostyril derivative represented by formula (1)

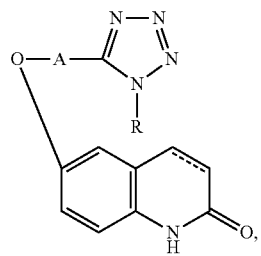

wherein R is a cycloalkyl group, A is a lower alkyl group, and a single bond or a double bond is present between the 3-position and the 4-position of the carbostyril nucleus, or a salt thereof, and (b) an effective amount of dihydroquercetin or a salt thereof.

8. The method according to claim 7, wherein the carbostyril derivative is 6-[4-(1-cyclohexyl-1H-tetrazol-5-yl)butoxy]-3,4-dihydrocarbostyril.

9. The method according to claim 7, wherein the dementia is Alzheimer-type dementia, Lewy body dementia, frontotemporal dementia, cerebrovascular dementia, Parkinson's disease, Down's syndrome, or Huntington's disease.

* * * * *